(12) United States Patent
Bellamy et al.

(10) Patent No.: US 6,361,642 B1
(45) Date of Patent: *Mar. 26, 2002

(54) HEAT AND PRESSURE-FORMED FLEXIBLE CONTAINERS

(75) Inventors: David Bellamy, Kenilworth; Ludwig Wolf, Jr., Barrington, both of IL (US)

(73) Assignee: Baxter International Inc., Deerfield, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/982,758

(22) Filed: Dec. 2, 1997

(51) Int. Cl.[7] .............................................. B32B 31/04
(52) U.S. Cl. ...................... 156/245; 156/285; 156/292; 156/308.4
(58) Field of Search ........................... 383/38; 264/545, 264/574, 573, 512, 516, 524, 535, 544, 572; 156/221, 222, 224, 292, 156, 245, 285, 287, 303.1, 306.6, 308.4

(56) References Cited

U.S. PATENT DOCUMENTS

| | | |
|---|---|---|
| 699,778 A | 5/1902 | Uphan |
| 1,374,088 A | 5/1921 | Miller |
| 3,576,650 A | 4/1971 | Underwood et al. |
| 3,616,033 A | 10/1971 | Blentarp |
| 3,654,012 A | 4/1972 | Schlager |
| 3,727,788 A | 4/1973 | Holbrook |
| 3,755,040 A | 8/1973 | Robinson |
| 3,783,870 A * | 1/1974 | Schachet .................... 604/321 |
| 3,801,402 A * | 4/1974 | Suter ........................ 156/182 |
| 3,861,977 A | 1/1975 | Wiley |
| 3,911,918 A * | 10/1975 | Turner ....................... 604/410 |
| 4,004,322 A | 1/1977 | Spendlove |
| 4,004,975 A | 1/1977 | Lionetti et al. |
| 4,076,063 A | 2/1978 | Cammarata et al. |
| 4,105,730 A | 8/1978 | Cammarata et al. |
| 4,116,338 A | 9/1978 | Weichselbaum |
| 4,222,379 A | 9/1980 | Smith |
| 4,244,364 A | 1/1981 | Grushkin |
| 4,253,458 A | 3/1981 | Bacehowski et al. |

(List continued on next page.)

FOREIGN PATENT DOCUMENTS

| | | |
|---|---|---|
| CA | 455916 | 4/1949 |
| DE | 2343453 | 9/1975 |
| JP | 3197031 | 12/1989 |
| WO | WO96/17514 | 12/1994 |

OTHER PUBLICATIONS

Korbling, M. et al., Description of a Closed Plastic Bag System for the Collection and Cryopreservation of Leukapheresis–Derived Blood Mononuclear Leukocytes and CFUc from Human Donors, Transfusion, May/Jun. 1980, PP 293–300.

Rubinstein MD, Pablo et al., Placental & Umbilical Cord Blood Banking for Unrelated Marrow Reconstitution, 1995 American Association of Blood Banks.

*Primary Examiner*—Michael W. Ball
*Assistant Examiner*—Gladys Piazza
(74) *Attorney, Agent, or Firm*—Daniel D. Ryah; Denise M. Serewicz; Amy L. H. Rockwell

(57) ABSTRACT

A flexible container comprises first and second flexible sheets of plastic material having peripheral edges, which have been sealed together along a plane to create an interior chamber in the container. At least one of the first and second flexible sheets includes a preformed, stress-relieved region, which is extended outside the plane and overlies at least a portion of the interior chamber.

4 Claims, 14 Drawing Sheets

U.S. PATENT DOCUMENTS

| | | | |
|---|---|---|---|
| 4,294,247 A | | 10/1981 | Carter et al. |
| RE31,135 E | | 2/1983 | Winchell et al. |
| 4,453,940 A | | 6/1984 | Aoyagi et al. |
| 4,460,365 A | | 7/1984 | Ganshirt et al. |
| 4,479,918 A | | 10/1984 | Hoeppel |
| 4,484,920 A | * | 11/1984 | Kaufman et al. ............ 604/416 |
| 4,505,708 A | | 3/1985 | Gajewski et al. |
| 4,519,796 A | * | 5/1985 | Russo ......................... 604/319 |
| 4,550,825 A | | 11/1985 | Sutryn |
| 4,588,401 A | | 5/1986 | Kilkson |
| 4,588,554 A | | 5/1986 | Kaartinen |
| 4,613,640 A | | 9/1986 | Deisler et al. |
| 4,619,650 A | * | 10/1986 | Wisdom ..................... 604/408 |
| 4,630,448 A | | 12/1986 | Bilstad et al. |
| 4,645,482 A | | 2/1987 | Yoshida |
| 4,657,542 A | | 4/1987 | Ohachi |
| 4,670,013 A | | 6/1987 | Barnes et al. |
| 4,714,680 A | | 12/1987 | Civin |
| 4,747,844 A | * | 5/1988 | Elliot ......................... 604/319 |
| 4,820,297 A | | 4/1989 | Kaufman et al. |
| 4,822,346 A | * | 4/1989 | Elliot ......................... 604/319 |
| 4,854,737 A | | 8/1989 | Steer et al. |
| 4,910,147 A | | 3/1990 | Bacehowksi et al. |
| 4,915,847 A | | 4/1990 | Dillon et al. |
| 4,937,194 A | | 6/1990 | Pattillo et al. |
| 4,994,021 A | | 2/1991 | Smith et al. |
| 4,997,083 A | | 3/1991 | Loretti et al. |
| 5,004,681 A | | 4/1991 | Boyse et al. |
| 5,018,622 A | | 5/1991 | Harltey |
| 5,038,938 A | | 8/1991 | Berndt |
| 5,045,076 A | | 9/1991 | Pierce |
| 5,053,025 A | | 10/1991 | Knippscheer |
| 5,055,198 A | | 10/1991 | Shettigar |
| 5,061,620 A | | 10/1991 | Tsukamoto et al. |
| 5,066,290 A | | 11/1991 | Measells et al. |
| 5,100,401 A | | 3/1992 | Patel |
| 5,114,421 A | | 5/1992 | Polak |
| 5,114,672 A | | 5/1992 | Knippscheer et al. |
| 5,135,762 A | | 8/1992 | Vernon et al. |
| 5,163,554 A | | 11/1992 | Lampropoulos et al. |
| 5,171,234 A | | 12/1992 | Jepson et al. |
| 5,171,527 A | | 12/1992 | Knippscheer et al. |
| 5,176,258 A | | 1/1993 | Antal |
| 5,188,620 A | | 2/1993 | Jepson et al. |
| 5,192,553 A | | 3/1993 | Boyse et al. |
| 5,226,564 A | | 7/1993 | Steer et al. |
| 5,257,983 A | | 11/1993 | Garyantgs et al. |
| 5,300,059 A | | 4/1994 | Rubinstein et al. |
| 5,306,269 A | | 4/1994 | Lewis et al. |
| 5,348,549 A | | 9/1994 | Brown et al. |
| 5,356,373 A | | 10/1994 | Dracker |
| 5,375,701 A | | 12/1994 | Hustad et al. |
| 5,379,895 A | | 1/1995 | Foslien |
| 5,411,499 A | | 5/1995 | Dudar et al. |
| 5,423,794 A | | 6/1995 | Adolf et al. |
| 5,439,100 A | | 8/1995 | Gordon et al. |
| 5,460,625 A | | 10/1995 | Johnson |
| 5,474,169 A | | 12/1995 | Bauman |
| 5,485,919 A | | 1/1996 | Samberg et al. |
| 5,486,390 A | | 1/1996 | Burns et al. |
| 5,622,867 A | | 4/1997 | Livesey et al. |
| 5,789,147 A | | 8/1998 | Rubinstein et al. |
| 5,871,477 A | * | 2/1999 | Isono et al. .................. 604/410 |
| 5,954,958 A | | 9/1999 | Folden |
| 6,213,334 B1 | | 4/2001 | Coelho et al. |

\* cited by examiner

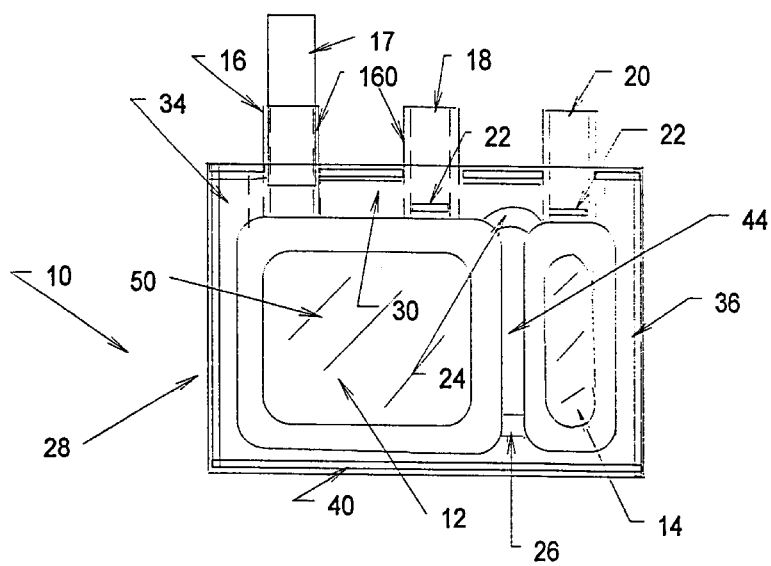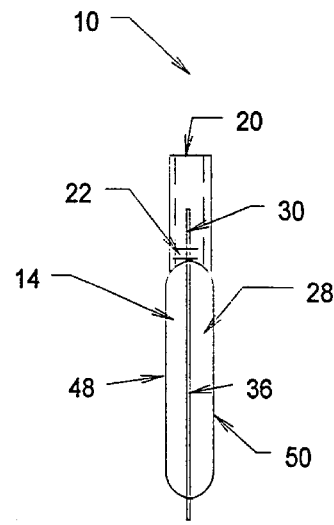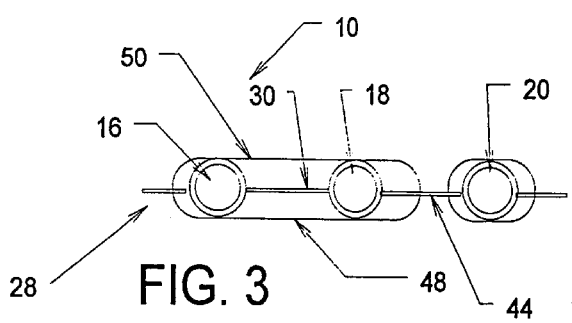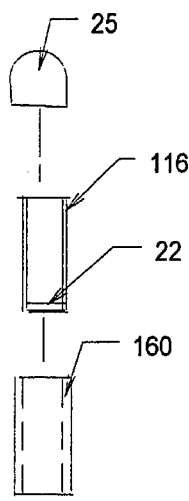
FIG. 1
FIG. 2
FIG. 3
FIG. 4

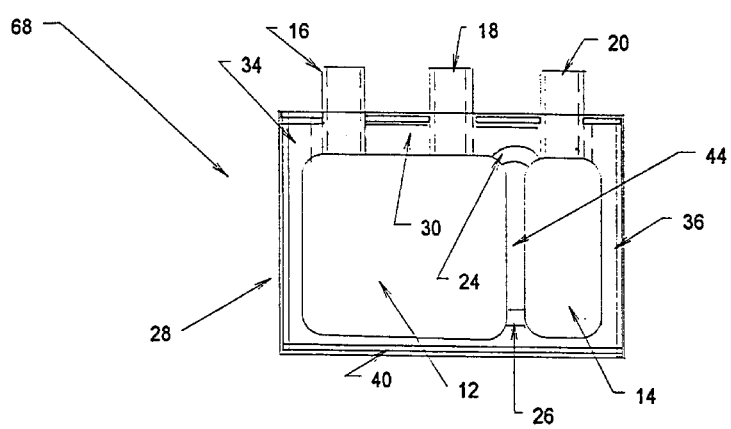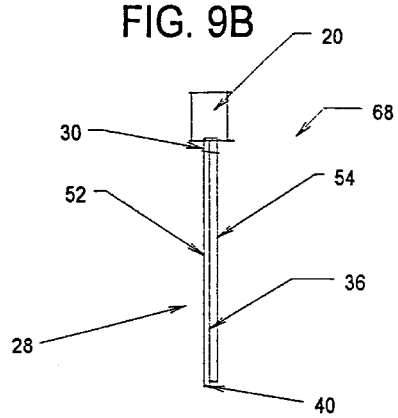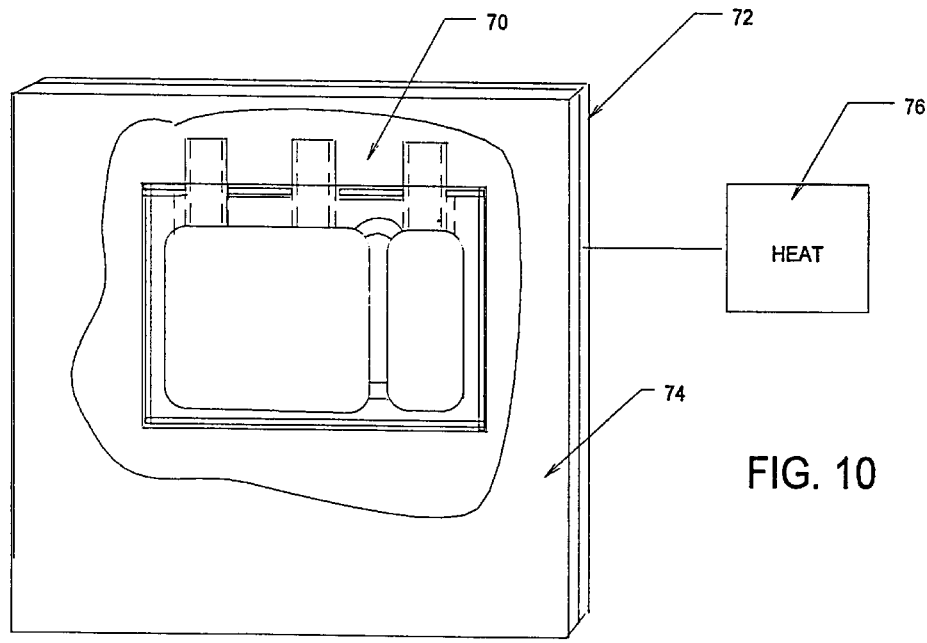

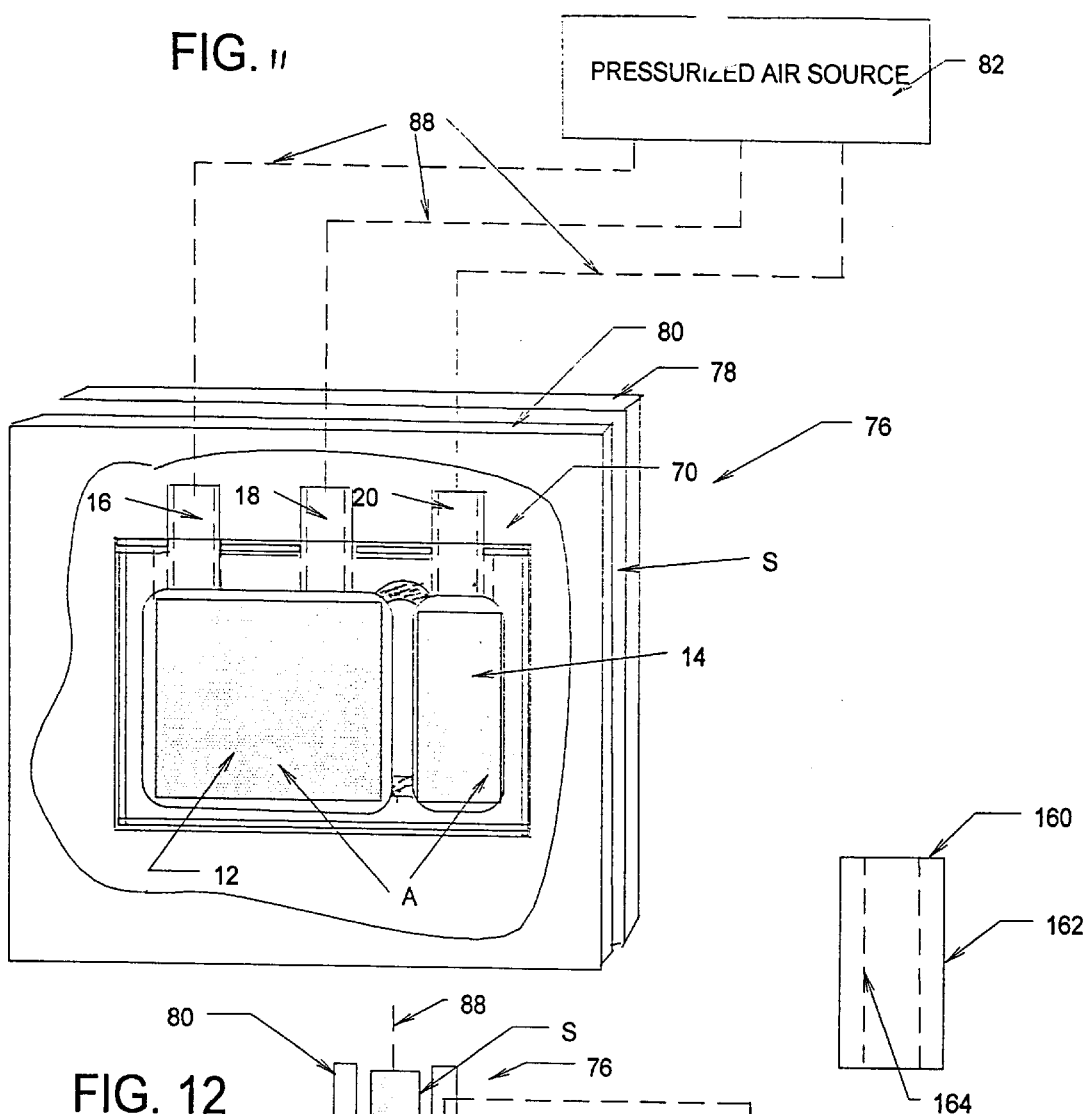
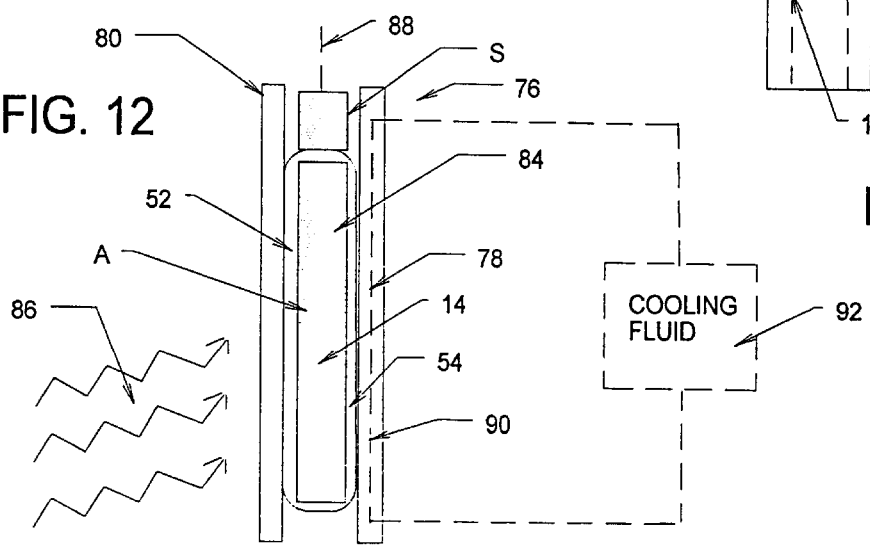
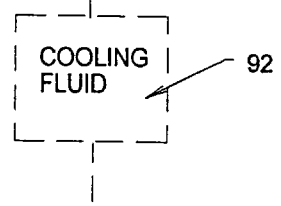

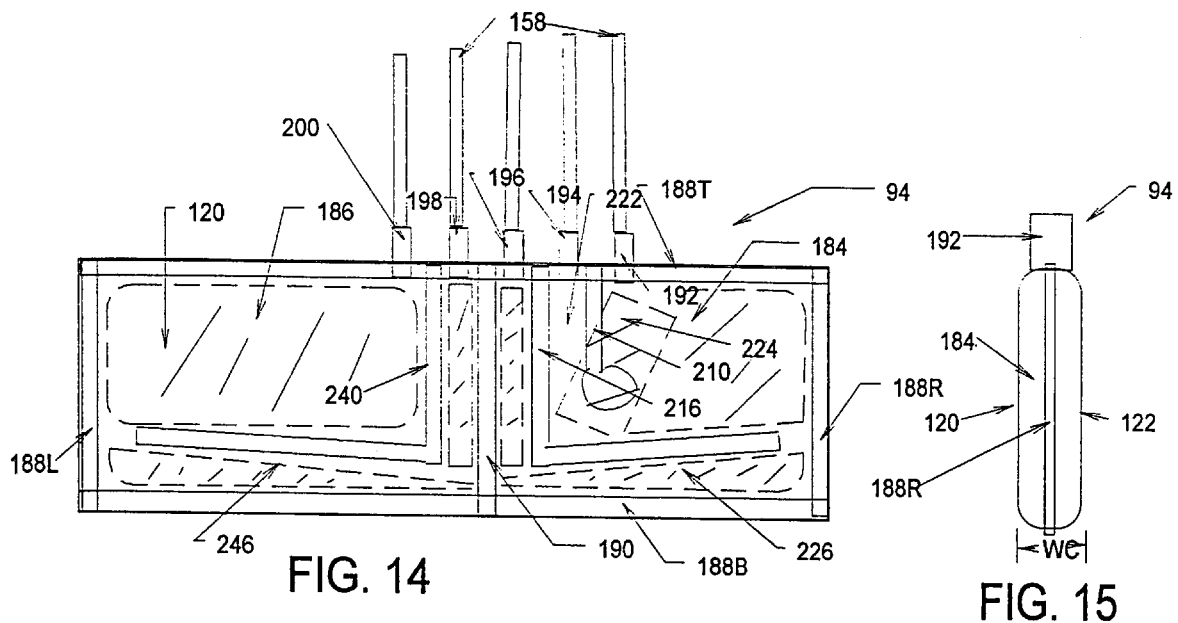
FIG. 14
FIG. 15
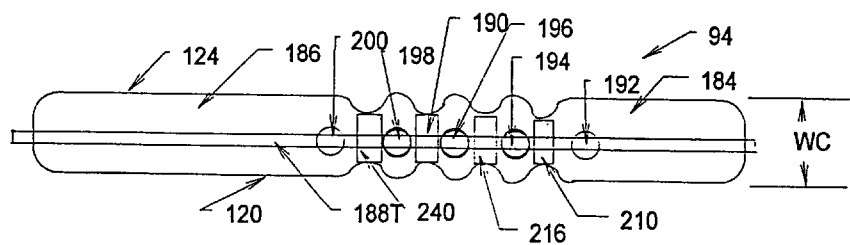
FIG. 16

HEAT AND PRESSURE-FORMED FLEXIBLE CONTAINERS

FIELD OF THE INVENTION

The invention relates to flexible containers and to processes by which these containers are made. In a more particular sense, the invention relates to flexible containers and associated manufacturing processes having attributes well suited for use in the medical field.

BACKGROUND OF THE INVENTION

Flexible containers for use in the medical field to process or store blood and tissue are well known. These containers are typically "lay flat" bags, formed by heat sealing flat sheets of medical grade plastic material together, with access ports, about their peripheral edges. These bags are ideally suited for many uses in the medical field.

Still, the opposite sheets of flexible plastic that make up the walls of these bag are subject to non-uniform deformation during use. That is, the sheeting deforms non-uniformly depending upon the orientation of the bags and the location of materials within the bags, so that one area of the bag will have a different geometry than another. For example, the bottom of the bag, in which the materials naturally accumulate by gravity, will be wider than the top of the bag, which is normally free of materials. This disparity in the distribution of stress can lead to localized failures and leaks. Because of the non-uniform deformation, these bags are also not well suited for measuring precise fluid volumes.

It is possible to form bags having three-dimensional geometries using blow molding. However, blow molding requires the extrusion of parisons before the blow molding process. Furthermore, the porting of blow molded containers can pose problems.

It is also possible to form bags having three-dimensional geometries using vacuum molding techniques. However, these techniques required specialized vacuum molding tools and equipment and specialized heat sealing dies and procedures. Furthermore, vacuum forming can weaken a sheet of plastic by stretching the plastic material in nonuniform manner, creating areas where the film has been overstretched and prone to failure when stressed.

SUMMARY OF THE INVENTION

The invention provides flexible, three-dimensional containers, which possess relatively precise, predefined geometries that are maintained during use. The invention also provides an assembly process by which flexible, three-dimensional containers can be made that meet exacting size and volume requirements, without the shortcomings of prior blow molded or vacuum formed containers.

One aspect of the invention provides a flexible container comprising first and second flexible sheets of plastic material having peripheral edges, which have been sealed together along a plane to create an interior chamber in the container. At least one of the first and second flexible sheets includes a preformed, stress-relieved region, which extends outside the plane and overlies at least a portion of the interior chamber.

In a preferred embodiment, containers that embody features of the invention are formed from first and second lay-flat sheets of plastic material, which can be softened by exposure to heat. The peripheral seal joins the two lay-flat sheets together along the plane, forming the interior chamber. The plastic material of the sheets has been extended or expanded into a preformed shape, which lies outside the plane, by the application of heat while positive pressure is applied to the interior chamber. The extension of the heat-softened material in response to positive pressure uniformly relieves material stress in the sheets. The combination of heat and positive pressure creates a robust container more resistant to stress-related material fatigue or failure than conventional lay-flat bags or bags having vacuum formed sides.

Other features and advantages of the inventions are set forth in the following Description and Drawings, as well as in the appended claims.

BRIEF DESCRIPTION OF THE DRAWINGS

FIG. 1 is a front view of a flexible three-dimensional container, which embodies features of the invention;

FIG. 2 is a right side elevation view of the container shown in FIG. 1;

FIG. 3 is a top view of the container shown in FIG. 1;

FIG. 4 is an exploded side view of a port tube assembly, which the container shown in FIG. 1 incorporates;

FIG. 9A is a front view of the second bag subassembly after the heat sealing operation shown in FIG. 8;

FIG. 9B is a side view of the second bag subassembly, showing its lay-flat configuration;

FIG. 10 is a front, largely schematic view of a fixture to heat the second bag subassembly to soften the plastic materials of its walls, thereby forming a third bag subassembly;

FIG. 11 is a front, largely schematic view of a fixture to apply pressure to the interior of the third bag subassembly, while the plastic materials of its walls are in a heat-softened condition;

FIG. 12 is a side view of the fixture shown in FIG. 11, showing a fourth bag subassembly, in which the heat-softened walls have been extended to a three-dimensional shape defined by the fixture;

FIG. 13 is an elevation view of a port tube for the container shown in FIG. 1, formed of two plastic materials;

FIG. 14 is a front view of an other flexible three-dimensional container, which embodies features of the invention, and which, in use, is a centrifugal blood processing chamber;

FIG. 15 is a right side elevation view of the container shown in FIG. 14;

FIG. 16 is a top view of the container shown in FIG. 14;

Figure 6:
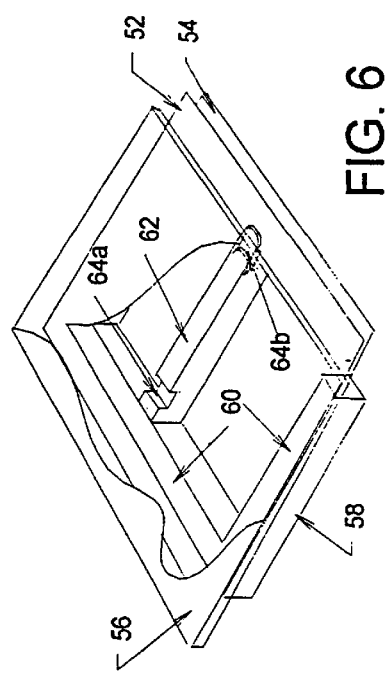
FIG. 6 is a perspective view of the two lay-flat plastic sheets being heat sealed together about their side and bottom edges to form a first bag subassembly.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The invention provides a flexible container characterized by a uniformly extended, three-dimensional geometry that provides improved resistance to pressure and stress failure. The geometry, when empty, provides a formed interior volume, which can be simple or complex. The geometry can, for example, provide interior compartmentalization, multiple interior flow passages, and diverse geometries (either curvilinear, or rectilinear, or both) with diverse dimensions (large or small).

I. Multiple Chamber, Blood storage Bag

FIGS. 1 to 3 show a representative embodiment of a heat and pressure-formed, flexible container 10, which embodies features of the invention. In this embodiment, the container 10 takes the form of a multiple chamber bag that is particularly well suited for use in the medical field to process or store blood constituents or tissue. However, the bag 10 is capable for use in many diverse environments.

A. Structure of the Bag

The bag 10 shown in FIGS. 1 to 3 is intended to receive a relatively small volume of blood constituent for storage at cryogenic temperatures. A representative embodiment of a bag intended for this use measures about 3.5 inches in width, about 3.0 inches in height, and about 0.25 to 0.50 inch in thickness.

Because of the contemplated end use, the bag 10 is made from materials having low glass transition temperatures, so that the bag can withstand cryogenic temperatures. Examples of such materials include polyethylene, polypropylene, ethylene-vinyl-acetate, fluropolymers, or copolymers of these materials. Of course, other materials can be used when other end uses are contemplated, which do not involve exposure to cryogenic temperatures.

As illustrated in FIGS. 1 to 3, the bag 10 includes two interior compartments 12 and 14. As FIG. 1 shows, the compartments 12 and 14 are of different sizes. Of course, the bag 10 can include a single compartment, or other multiple compartments having different geometries.

Multiple ports 16, 18, and 20 individually service the compartments 12 and 14. Two ports 16 and 18 communicate with the first compartment 12. One port 20 communicates with the second compartment 14. Of course, more or fewer ports can be provided, according to the requirements dictated by the intended use.

In the illustrated and preferred embodiment, the port 16 is coupled to a length of flexible tubing 17. The tubing 17 carries at its free end a suitable sterile or aseptic connection device (not shown), to establish communication with a source of material that is to be conveyed into the bag compartment 12. Once the material is transferred into the compartment 12, the tubing 17 can be closed by a conventional radio frequency heat seal, which permits tubing 17 beyond the seal to be disconnected from the bag 10.

In the illustrated and preferred embodiment, the ports 18 and 20 each carry within them a pierceable membrane 22. The membranes 22 normally close the ports 18 and 20 to fluid flow. In use, the membranes 22 are opened by conventional pointed cannulas, or "spikes", which are well known in the medical field. The pointed cannulas are typically carried by flexible tubing to channel material into or out of the bag compartments 12 or 14. As FIG. 4 shows, a removable cap 25 preferably closes the end of the ports 18 or 20 before use.

The composite bag 10 also includes interior fluid passages 24 and 26. The passages 24 and 26 permit fluid (gas and liquid) flow between the interior compartments 24 and 26 during use. For example, a sample of the material can be conveyed from the compartment 12 into the compartment 14 through the interior passages 24 and 26.

As FIG. 1 shows, the bag includes an upper interior passage 24 and a lower interior passage 26. The bag 10 may include more or fewer or no interior passages.

The composite bag 10 includes a continuous peripheral seal 28. The continuous peripheral seal 28 includes an upper region 30, which seals the ports 16, 18, and 20 to the bag 10. The upper seal region 30 also seals the top edges of the two compartments 12 and 14.

The peripheral seal 28 also includes a left seal region 34 and a right seal region 36. The left and right seal regions 34 and 36 seal, respectively, the side edges 38 of the first and second compartments 12 and 14.

The peripheral seal 28 further includes a bottom seal region 40. The bottom seal region 40 seals the bottom edges of the two compartments.

An interior seal region 44 seals the interior edges of the first and second compartments 12 and 14. Spaced apart interruptions in the interior seal 44 form the upper and lower interior passages 24 and 26, already described.

The peripheral seal 28 and interior seal 44 creates a leakproof barrier for the ports 16, 18, and 20 and the compartments 12 and 14, except where purposely interrupted to form the upper and lower interior passages 24 and 26.

The passages 24 and 26 can be sealed during use using a conventional hand-held sealer, for example, the SEBRA™ sealer Model 1090, made and sold by Engineering Research Associates (Tucson, Ariz.). As FIG. 1 shows, the upper interior passage 24 extends in an arcuate path toward the upper seal region 30 of the bag 10. This arcuate path positions the passage 24 very closely to the top peripheral edge of the bag. Likewise, in FIG. 1, the lower interior passage 26, while not extending in an arcuate path, is nevertheless also positioned close to the bottom peripheral edge of the bag 10. This positioning makes the passages easily accessed for sealing using a conventional hand-held RF sealer.

In addition, the interior seal 44 possesses a width sufficient to distance the compartments 12 and 14 away from unintended electric heat effects during use, caused by proximity to hand-held heat sealing tools. The width dimension of the interior seal depends upon the dimensions and geometry of the sealing tool used. For example, a Model 1090 SEBRATM tool uses a cylindrical heating electrode that is about ⅜ inch in diameter. It has been determined that this heating electrode will cause unintended heating effects in the material of the compartments 12 and 14 when the interior seal 44 is about ⅛ inch in width. However, when the interior seal 44 is increased to a width of ¼ inch, these unintended heating effects are eliminated.

As FIGS. 2 and 3 best show, the front wall 48 and the back wall 50 of the bag 10 extend, when the bag 10 is empty, outwardly beyond the plane peripheral seal 28, forming a generally convex or bowed, dome shape. The preformed walls 48 and 50, joined together by the peripheral and interior seals 28 and 44, provide a three-dimensional, yet flexible geometry.

Figure 5:
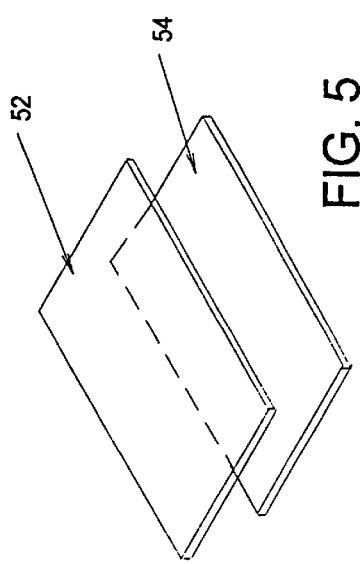
FIG. 5 is a perspective view of two lay-flat sheets of plastic material from which the walls of the container shown in FIG. 1 are made.

B. Assemblage of The Bag (i) First Phase: Formation of Side, Bottom, and Interior Seals in Lay-Flat Walls The bag 10 is formed from two, initially lay-flat sheets 52 and 54 of material of the selected plastic composition. FIG. 5 shows the lay-flat sheets 52 and 54 before assembly into the bag 10.

In assembling the bag 10 (see FIG. 6), the lay-flat sheets 52 and 54 are first sealed together along their side and bottom edges using conventional heat sealing dies 56 and 58. In the illustrated embodiment, the dies 56 and 58 are made of materials capable of transmitting radio frequency energy, such as brass or aluminum. The material for the dies 56 and 58 be coated, e.g., the material can comprise anodized aluminum, or have a release agent coating, such as TEFLON™ plastic.

Radio frequency energy is transmitted by raised surfaces 60 of the die 58 to electrically heat the edges of plastic sheets 52 and 54, which are sandwiched between the opposing dies 56 and 58. Heating forms the left, right, and bottom seal regions 34, 36, and 40. Raised surface 62 of the die 58 electrically heats interior portions of the two sheets 52 and 54, thereby forming the interior seal region 44. The surface is interrupted in regions 60a and 60b to form the interior passages 24 and 26.

Figure 7:
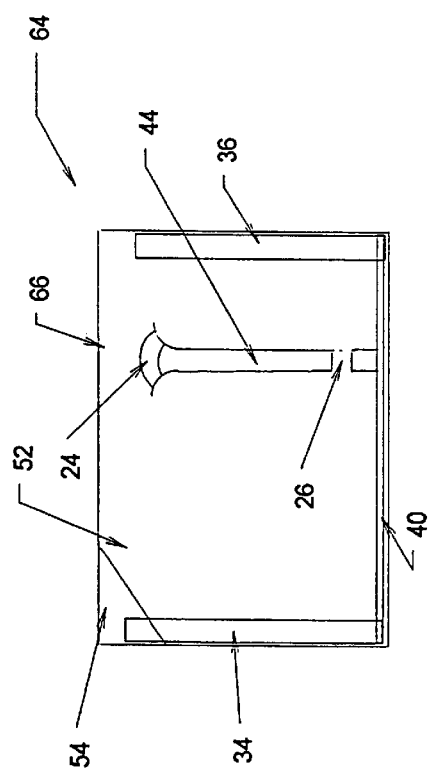
FIG. 7 is a front view of the first bag subassembly after the heat sealing operation shown in FIG. 6.

FIG. 7 shows the first stage bag subassembly 64, which comprises the two lay-flat sheets 52 and 54 heat sealed together, forming the left, right, bottom, and interior seal regions 34, 36, 40, and 44, together with passages 24 and 26. The top edges 66 of the first stage bag subassembly 64 are left unsealed and open at this phase of the assembly.

(ii) Second Phase: Formation of Top and Port Seals in Lay-Flat Walls

Figure 8:
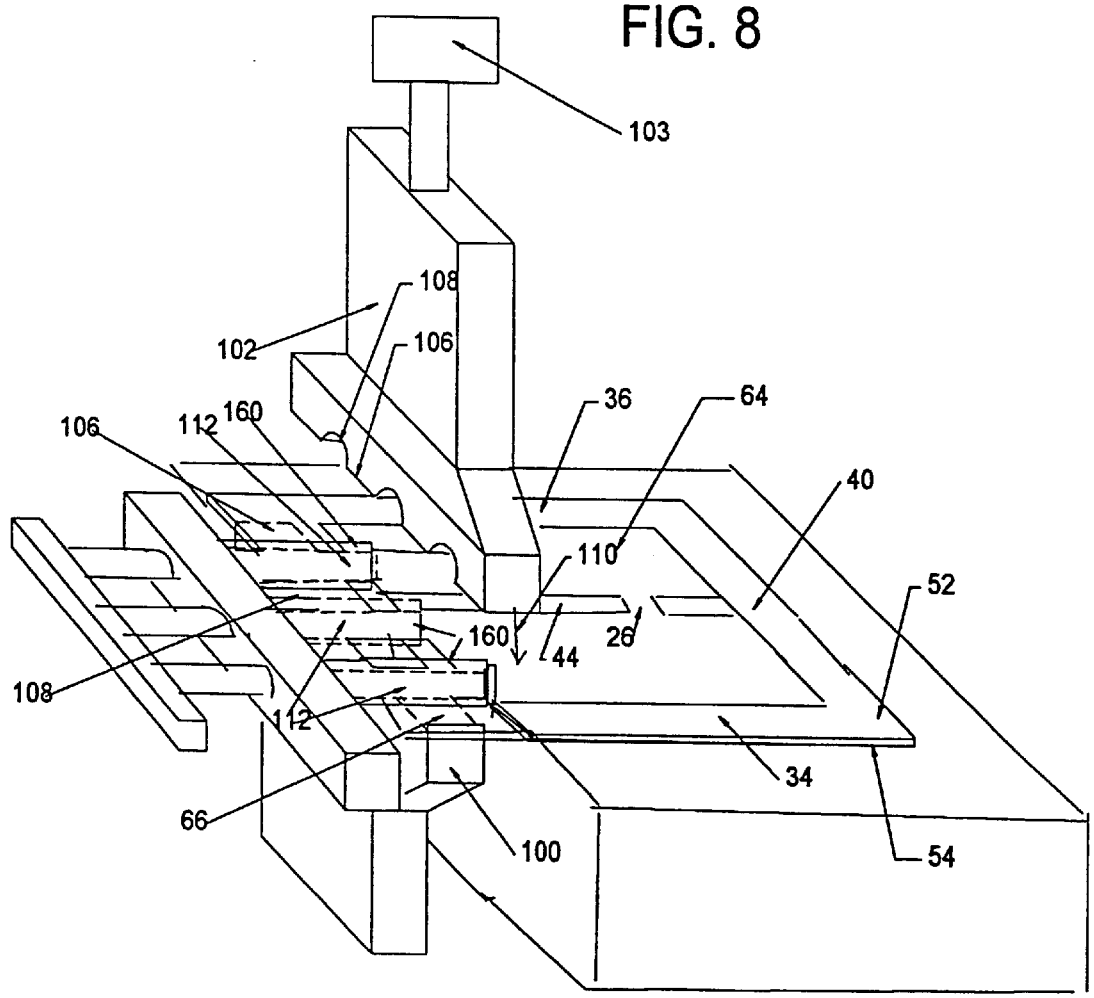
FIG. 8 is a perspective view of the operation of heat sealing the port tubes to the top edge of the first bag subassembly, to forth a second bag subassembly.

As FIG. 8 shows, assembly of the bag 10 next entails placing the top edges 66 of the first stage bag subassembly 64 between mating first and second sealing fixtures 100 and 102. FIG. 8 shows the fixtures 100 and 102 in a spaced apart condition for the purpose of illustration. Each fixture 100 and 102 includes a planar surface 106 with spaced-apart recesses 108. A ram 103 moves the fixture 102 down upon the fixture 100, as indicated by the arrow 110 in FIG. 8. When the fixtures 100 and 102 are mated, the recesses 108 coincide to form 360° cylindrical passages.

An array of spaced-apart mandrels 112 nest within the recesses 108. The mandrels 112 each receives a port tube 160, which forms the core of the respective bag port (see FIG. 4). The port tubes 160 are made of a plastic material, at least the outer surface of which is compatible with the material of the sheets 52 and 54, to permit heat sealing.

The fixtures 100 and 102 and the mandrels 112 are made of materials, previously described, capable of transmitting radio frequency energy, and be coated. Radio frequency energy is applied to the mandrels 112 for return through the fixtures 100 and 102, which are electrically coupled to RF ground.

The radio frequency energy electrically heats the materials of the port tubes 116 and adjoining sheets 52/54 surrounding the port tubes 116. The materials in this heated zone soften and flow together, joining the port tubes 116 to the sheets 52/54. The mandrels 112 keep the port tubes 116 open and in a round configuration during the process.

The heated plastic is allowed to cool and set under the pressure exerted by the ram 103 upon the fixtures 100 and 102. The electric heating and consequent flow of materials captured by the fixtures 100 and 102 create the upper seal region 30. Here, the flow of materials also joins the exterior of the port tubes 116 between the adjacent materials of the sheets 52/54.

This completes the formation of the second stage bag subassembly 68(see FIGS. 9A and 9B), which comprises the two lay flat sheets 52 and 54 with an entire peripheral seal 28 and interior seal 44 formed, and with the ports 16, 18, and 20 attached. The ports 16, 18, and 20 do not include a pierceable membrane 22, which is inserted at a later phase of assembly. The ports 16, 18, and 20 are thereby open for the introduction of a pressurized fluid at a later phase of assembly, as will be described.

(iii) Third Phase: Softening the Lay-Flat Wall Material by Heat

Assembly of the bag 10 next entails heating the second stage bag subassembly 68 to a temperature above room temperature, where the material from which the plastic sheets 52 and 54 is made begins to soften.

The range of temperatures in which softening occurs will depend upon the particular composition of the plastic used. For example, for polyethylene, ethylene-vinyl-acetate, fluropolymers, or copolymers of these materials, the softening temperature lays in the range of about 80° C. to about 90° C. For polyvinyl chloride and polypropylene plastic materials, the softening temperature lays in the range of about 110° C. to about 130° C. An operating range of softening temperatures for a given plastic material can be empirically determined.

FIG. 10 shows a third stage bag subassembly 70, which is suspended between two radiant heating plates 72 and 74, coupled to a heart source 76. Alternatively, the heating can be accomplished using a convection oven or a hot air stream. The plastic material of the sheets 52 and 54 softens in response to the applied heat.

(iv) Fourth Phase: Extending or Expanding the Wall Material by Interior Pressure While in a heat-softened state, the third stage bag subassembly 70 is moved from the heating plates 72 and 74 and placed in a restraining fixture 76. As FIG. 11 shows, the restraining fixture 76 consists of opposed parallel plates 78 and 80, which are maintained at room temperature (i.e., at a temperature cooler than the third stage bag subassembly 70). The parallel plates 78 and 80 form a predefined space S between them, which is larger than the thickness of the lay-flat geometry of the third stage bag subassembly 70 (which FIG. 9B shows). The third stage bag subassembly 70 is held within the space S by the parallel plates 78 and 80 along the upper seal region 30. The remainder of the peripheral seal 28 and interior seal 44 are not directly supported by the plates 78 and 80.

One or more of the ports 16, 18, and 20 are coupled by tubes 88 to a source 82 of pressurized fluid. Those ports 16, 18, or 20 that are not coupled to the source 82 are capped to retain pressurized fluid in the interior chambers 12 and 14. Preferably, the pressurized fluid is air, designated A in FIG. 11. The pressurized air A is introduced into the interior chambers 12 and 14 of the third stage bag assembly 70.

The magnitude of pressure will vary depending upon the physical characteristics of the plastic material and burst strength of the heat seals formed. For a typical bag, air pressure in the range of 5 to 10 psi can be used.

The introduction of pressurized air A into the chambers 12 and 14 causes the heat-softened sheets 52 and 54 to expand or billow outwardly (see FIG. 12). The space S within the fixture limits the extent to which the chambers 12 and 14 will expand. The third stage bag assembly 70 will, upon expansion, gradually conform to the space S within the fixture 76.

Because the third stage bag assembly 70 is supported only along the upper seal region 30 and is not otherwise asymmetrically confined in the space S, the material of both heat-softened sheets 52 and 54 will extend generally equally as it gradually expands to meet the generally symmetric limits of the fixture 76. Because the interior fluid pressure is applied uniformly along the entire unsealed area of the third stage bag assembly 70, the extension of the heat-softened material uniformly relieves material stress along the entire unsealed area, and the third stage bag assembly 70 acquires a new, symmetrically expanded shape, comprising a fourth stage bag assembly 84.

The dimension of the space S between the restraining fixture is selected based upon the final desired geometry of the bag 10, after assembly. One or both of the plates 78 and 80 of the fixture 76 can possess flat surfaces. Alternatively, one or both plates 78 and 80 can be contoured, if special wall contours are desired. Of course, the dimension of the space defined by the fixture 76 should not allow expansion of the heat-softened walls 52 and 54 to the extent that wall failure or seal bursting occurs.

(v) Fifth Phase: Cooling the Extended Wall Material

FIG. 12 shows a fourth stage bag subassembly 84, which has acquired the desired new shape between the two fixture plates 78 and 80 under the influence of internal pressurized air A. Assemblage of the bag 10 next entails allowing the fourth stage bag subassembly 84 to cool while still constrained the within the fixture 76 and subject the application of internal pressurized air A.

In this condition, the fourth stage bag subassembly 84 can be cooled by an ambient external air flow 86, or by a pressurized stream of cooling air. Alternatively, one or both plates 78 and 80 of the fixture 76 can include interior passages 90 (shown in phantom lines in FIG. 12) through which a cooling fluid can be circulated from a source 92 (also shown in phantom lines in FIG. 12), when cooling is desired. The speed at which cooling occurs affects the time of the overall assembly process.

When the fourth stage bag subassembly 84 has cooled to room temperature, the application of pressure is terminated and the fixture 76 is removed. The previous lay-flat bag subassemblies 68 and 70 have been transformed, through intermediate heated and extended subassembly 84, into to the bag 10 shown in FIG. 1. The bag 10 possesses a three-dimensional shape to possess a preformed, permanent interior volume.

(vi) Final Assembly and Sterilization

As FIG. 4 shows, after removal from the fixture, tubes 116, each carrying the previously described pierceable membrane 22 are inserted into the appropriate port tubes 160 and secured there using, for example, adhesive or a solvent. The tubing 17 is likewise secured by adhesive or solvent bonding to the appropriate port tube 160. As FIG. 4 also shows, the cap 25 is also be inserted on each port tube 160. The flexible, three-dimensional bag 10 has been created.

The bag 10 can be sterilized by conventional methods, without deformation. The manner of sterilization selected depends upon the materials that the bag 10 incorporates. For example, all plastic materials can undergo ethylene oxide (ETO) sterilization. Plastic materials, such as conventional medical grade polyvinylchloride, can also be sterilized by autoclaving. Other plastic materials, like ethylene-vinyl-alcohol, which melt at autoclaving temperatures, can be sterilized by exposure to gamma radiation.

Circumstances may give rise to material compatible issues. For example, material selected for the port tube 160 (for example, polyvinyl chloride) to allow adhesive or solvent sealing of the membrane tube 116 or the tubing 17 may not itself be heat sealable to the bag material (for example, if the bag 10 is made from ethylene-vinyl-alcohol). In such circumstances (see FIG. 13), the port tube 160 preferably comprises a coextrusion of two layers 162 and 164 of different materials. In the arrangement, the first material for the exterior layer 162 of the port tube 160 is selected to be heat sealable to the material of the bag 10 during the port sealing process described above. The second material for the interior layer 164 of the port tube 160 is selected to be solvent bonded to the material of the membrane tube 160 during final assembly of the bag 10, also as previously described. In the context of the example given above, the coextrusion for the port tube 160 comprises an outer layer 162 of ethylene-vinyl-alcohol material and an inner layer 164 of polyvinyl chloride.

II. Heat and Pressure-Formed Centrifugal Processing Chamber

Figure 17:
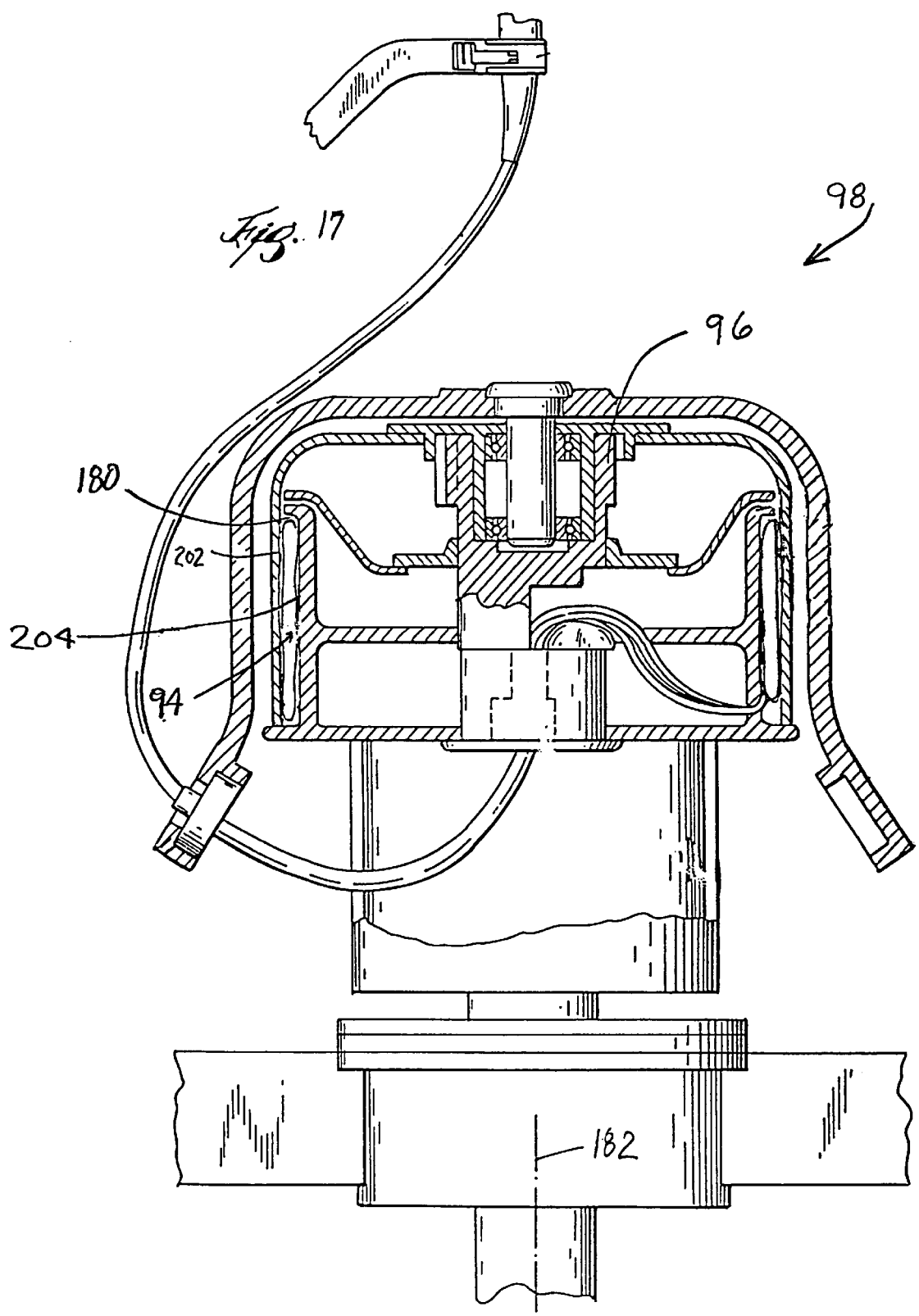
FIG. 17 is a side view of the container shown in FIG. 14 when mounted for use in a centrifuge rotor.

FIGS. 14 to 16 show another representative embodiment of a heat and pressure-formed, flexible container 94 having features of the invention. In this embodiment, the container 94 takes the form of an elongated, flexible blood processing container, which, in use, is carried for rotation on the rotor 96 of a centrifuge 98(see FIG. 17). Details of the centrifuge 98 and the mounting of the container 94 on the centrifuge rotor can be found in U.S. Pat. No. 5,370,802, entitled "Enhanced Yield Platelet Systems and Methods," and U.S. Pat. No. 5,360,542 entitled "Centrifuge With Separable Bowl and Spool Elements Providing Access to the Separation Chamber," which are each incorporated herein by reference.

A. Structure of the Container

As FIG. 14 best shows, the processing container 94 is divided into two side-by-side processing chambers 184 and 186. In use, centrifugal forces in the first chamber 184 separate whole blood into red blood cells (RBC) and platelet-rich plasma (PRP). Centrifugal forces in the second chamber 186 separate the PRP from the first stage into platelet concentrate (PC) and platelet-poor plasma (PPP).

Left, right, top and bottom peripheral seals, respectively 188L, 188R, 188T, and 188B form the outer edge of the container 94. A second, interior seal 190 divides the container into the first and second processing chambers 184 and 186. The second seal 190 extends generally parallel to the axis about which container 94 is rotated during use.

Five ports 192/194/196/198/200 open into the chambers 184 and 186. The ports 192/194/196/198/200 are arranged side-by-side along the top transverse edge of the respective chamber 184 and 186. Three ports 192/194/196 serve the first chamber 84. Two ports 198/200 serve the second chamber 86.

The first port 192 comprises a PRP collection port. The second port 194 comprises a WB inlet port. The third port 196 comprises a RBC collection port. The fourth port 198 constitutes a PPP collection port. The fifth port 200 constitutes a PRP inlet port.

Addition interior seals define various fluid pathways in the container 94. A third interior seal 210 is located between the PRP collection port 192 and the WB inlet port 194. A fourth interior seal 216 is located between the WB inlet port 194 and the RBC collection port 196. Together, the third and fourth interior seals 210 and 216 form a WB inlet passage 222 in the first chamber 184. The third interior seal 210 also forms a PRP collection region 224 within the first chamber 184.

Together, the fourth interior seal 216, the second interior seal 190, and the bottom peripheral seal 188B form a RBC collection passage 226, which communicates with the RBC collection port 196.

A fifth interior seal 240 extends between the PRP inlet port 200 and the PPP collection port 198. The fifth interior seal 240, the second interior seal 190, and the lower regions of the first peripheral seal 188 together form a PPP collection passage 246.

In use (see FIG. 17), the container 94, filled with blood, occupies an arcuate gap 180, which is formed in the rotating rotor 96 of the centrifuge 98. As also shown from the top in FIG. 18, the radial boundaries of the centrifugal field created in the container 94 during rotation of the rotor are formed by a high-G wall 202 and a low-G wall 204. The high-G wall 202 and the low-G wall 204 are typically contoured to enhance the separation conditions within the container 94.

Figure 18:
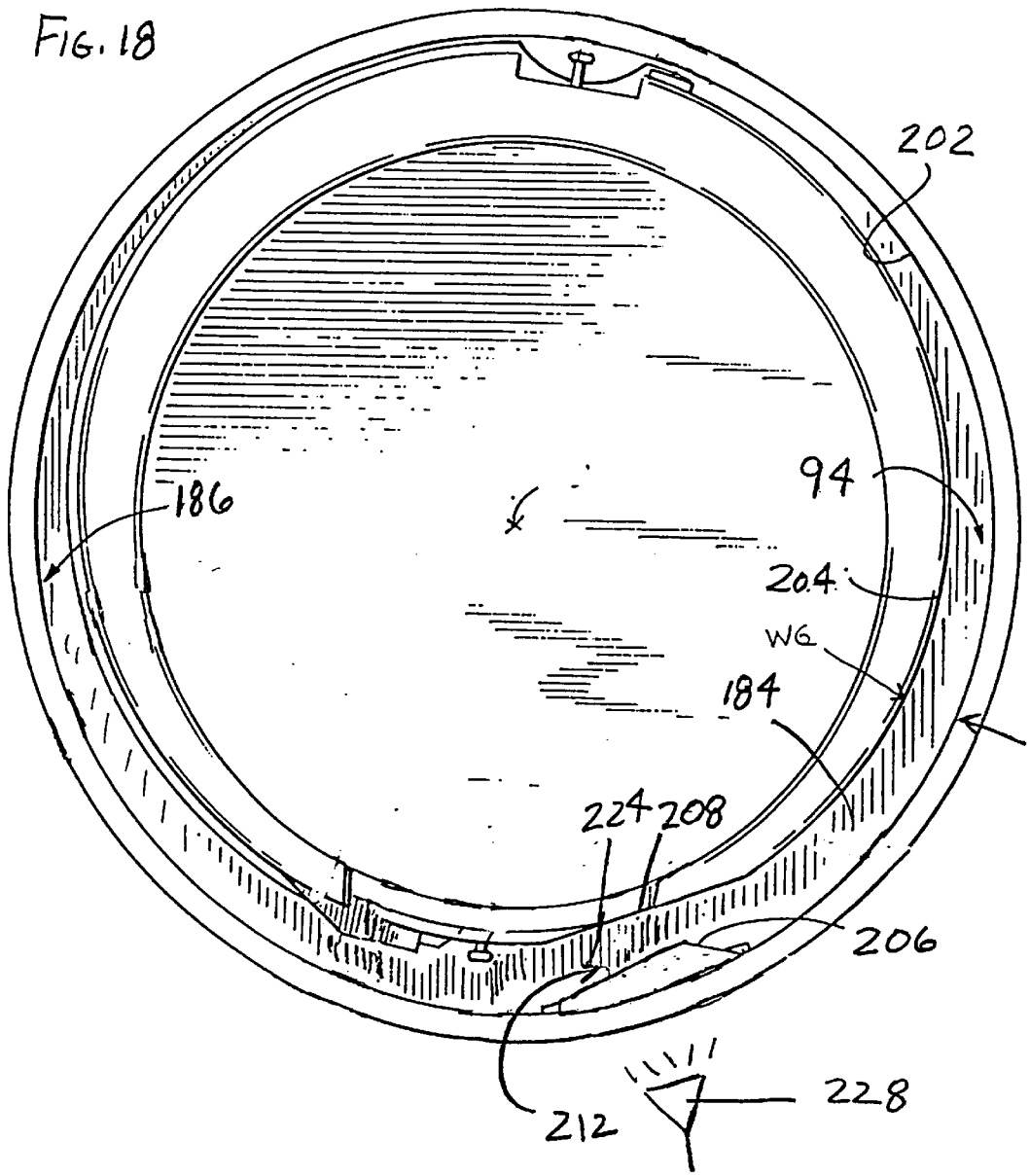
FIG. 18 is a top view of the centrifuge rotor shown in FIG. 17, showing contoured areas formed along the high-G and low-G walls.
Figure 19:
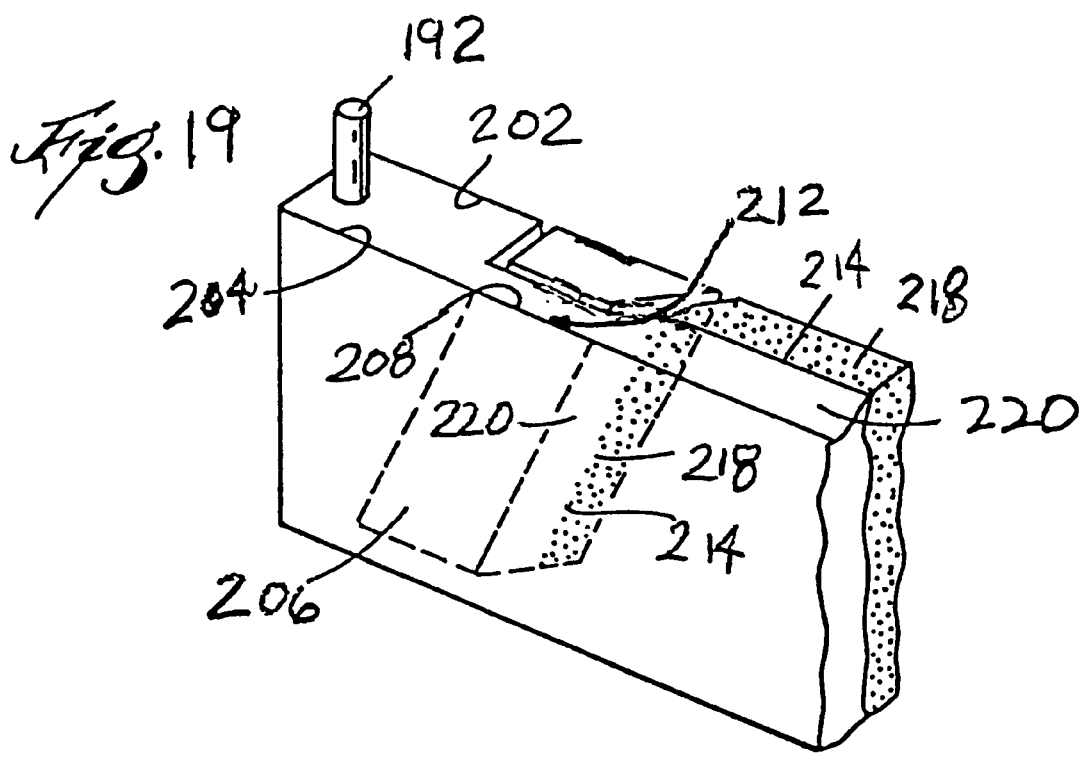
FIG. 19 is an enlarged, perspective view of one of the contoured areas shown in FIG. 18.

For example (see FIG. 18), in a preferred embodiment, the surface of the low-G wall 204 along the first compartment 184 is contoured to continuously change in terms of its radial distance from the rotational axis 182. Furthermore, in the PRP collection region 224 of the first compartment 184, the contour of the high-G wall 202 forms a tapered wedge 206. Radially across from the tapered wedge 206, the contour of the low-G wall 204 forms a flat surface 208. The tapered wedge 206 and the flat surface 208 form a constricted passage 212 along the low-G wall 204. As also shown in FIG. 19, the passage 212 diverts the fluid flow along the high-G wall 202 of the first compartment 184, to keep the interface 214 between the RBC 218 and PRP 220 away from the PRP collection port 192, while still allowing PRP 220 to reach the PRP collection port 192. As FIG. 19 shows, this flow diversion also changes the orientation of the interface 214, so that it can be display for viewing through a side wall of the container 94 by an associated interface controller 228 (see FIG. 15). This makes possible the control of the position of the interface 214 during processing. Details of a preferred embodiment for displaying and controlling the interface are described in U.S. Pat. No. 5,316,667, which is incorporated herein by reference.

As FIGS. 15 and 16 best show, the front wall 120 and the back wall 122 of the container 94 extend, when the container 94 is empty, outwardly beyond the plane of the peripheral seal 188L, 188R, 188T, and 188B, forming a generally convex or bowed, dome geometry, like the container 10 shown in FIGS. 1 to 3. The geometry of the container 94 has a width WC, when the container 94 is empty, that generally corresponds with the radial width WA of the arcuate gap 180 (see FIG. 18), which the container 94 occupies during centrifugation. Furthermore, the walls 120 and 122 have, through the application of heat and pressure, been uniformly extended to conform, when the container 94 is filled with blood, to the just described contours 206, 208, 210, and 212 of the high-G and low-G walls 202 and 204, without the creation of localized regions of material stress where the contours change. The container 94 therefore provides a three-dimensional, yet flexible geometry, which has been relieved of stress in the configuration it is expected to assume during use, when filled with blood.

Figure 20:
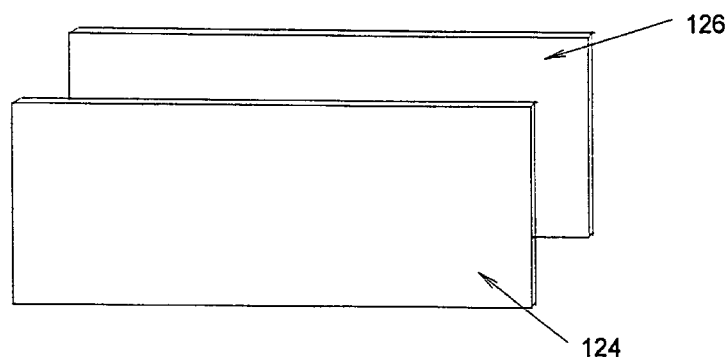
FIG. 20 is a perspective view of two lay-flat sheets of plastic material from which the walls of the container shown in FIG. 14 are made.

B. Assemblage of the Container (i) First Phase: Formation of Bide, Bottom, and Interior seals in Lay-Flat Walls Like the bag 10, the walls 120 and 122 container 94 is formed (see FIG. 20) from two elongated, initially lay-flat sheets 124 and 126 of material of the selected plastic composition. In the illustrated embodiment, the sheets can comprise medical grade plasticized polyvinlychloride (PVC) material. FIG. 20 shows the elongated lay-flat sheets before assembly into the container.

The elongated, lay-flat sheets 124 and 126 are first heat sealed together along their side and bottom edges to form the side and bottom portions of the main peripheral seal 188. Facing interior portions of the two elongated sheets 124 and 126 are also heat sealed together to form the interior seal regions 190, 210, 216, and 240. The elongated sheets 124 and 126 can be placed between conventional radio frequency sealing dies for this purpose, like the dies 56 and 58 shown in FIG. 6, with peripheral and interior radio frequency transmitting surfaces 60 and 62 patterned to match the location of the peripheral and interior seals of the container 94.

Figure 21:
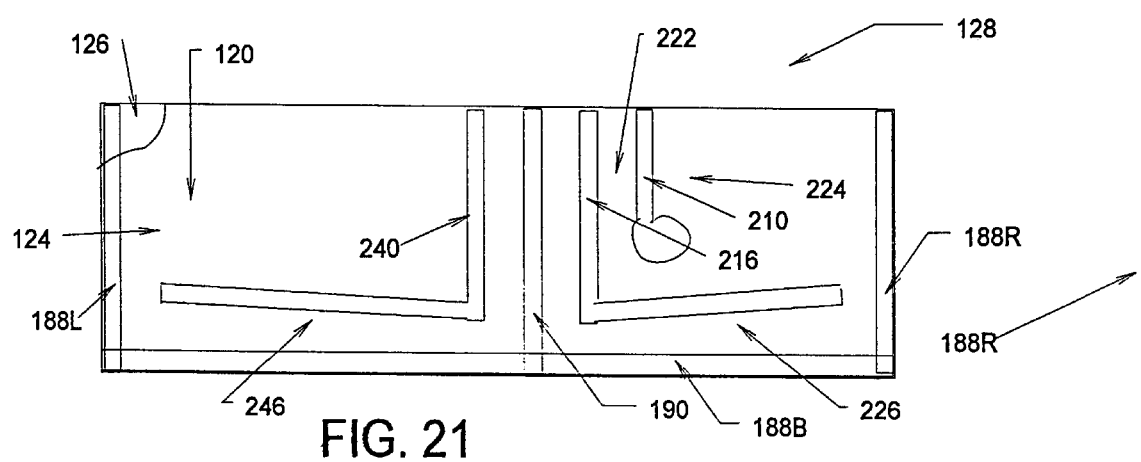
FIG. 21 is a front view of a first bag subassembly, in which the two lay-flat plastic sheets shown in FIG. 20 have been heat sealed together about their side and bottom edges.

FIG. 21 shows the first stage container subassembly 128 comprising the two lay-flat sheets 124 and 126 heat sealed together, forming the left, right, and bottom peripheral seals (designated, respectively, 188L, 188R, and 188B in FIG. 21), and the interior seal regions 190, 210, 216, and 240. The top edges 130 of the first stage container subassembly 128 are left unsealed and open at this phase of the assembly.

(ii) Second Phase: Formation of Top and Port Seals in Lay-Flat Walls

Figure 22A:
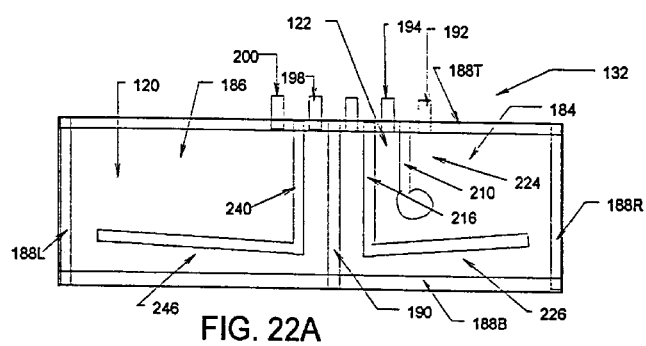
FIG. 22A is a front view of a second bag subassembly, in which the port tubes have been heat sealed to the top edge.
Figure 22B:
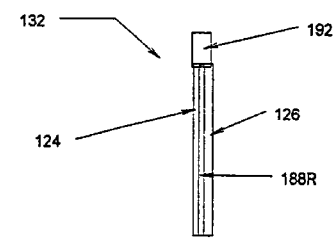
FIG. 22B is a side view of the second bag subassembly, showing its lay-flat configuration.

Assembly of the container 94 next entails the use of fixtures 100/102 and mandrels 112, like that previously described and shown in FIG. 8, to apply heat (e.g., by applying radio frequency energy) along the top edges 130 of the first phase container subassembly 128, to join the exterior of the port tubes 160 between the adjacent materials of the sheets 124 and 126 and form the top peripheral seal 188T. The resulting second stage container subassembly 132(see FIGS. 22A and 22B) comprises the two lay flat sheets 124 and 126 with an entire peripheral seal 188, all interior seals 190, 210, 216, and 240, and with all ports 192, 194, 196, 198, and 200 attached. The ports 192, 194, 196, 198, and 200 of the second stage container subassembly 132 are left open for the introduction of a pressurized fluid at a later phase of assembly, as will be described.

(iii) Third Phase: Softening the Lay-Flat Wall Material by Heat

Assembly of the container 94 next entails heating the second stage container subassembly 132 to a temperature above room temperature to soften the material from which the plastic sheets 124 and 126 are made. The temperature range for softening PVC material of the sheets lays between about 110° C. to about 130° C.

Figure 23:
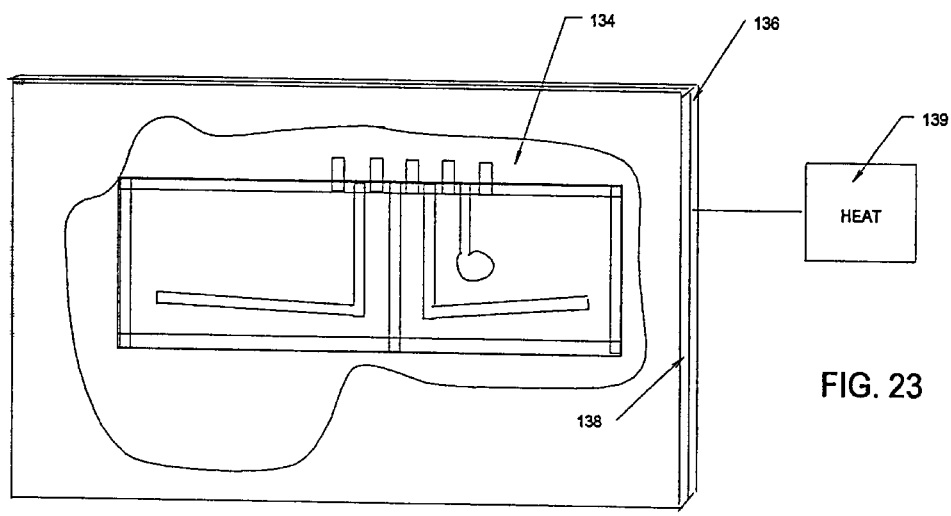
FIG. 23 is a front, largely schematic view of a fixture to heat the second bag subassembly shown in FIGS.22A and 22B to soften the plastic materials of its walls, thereby forming a third bag subassembly.

FIG. 23 shows a third stage container subassembly 134, suspended between two heating plates 136 and 138 (like those previously shown and described in connection with FIG. 10). The plates 136 and 138 are coupled to a heat source 139, as also already described. In the third stage container subassembly 134, the plastic material is softened by heat and ready for the next phase of the assembly process.

(iv) Fourth Phase: Extending or Expanding the Wall Material by Interior Pressure The third phase container subassembly 134, with the plastic sheets 124 and 126 in a heat-softened state, is moved from the heating plates 136 and 138 and placed in a restraining fixture 140 (see FIG. 24).

Figure 24:
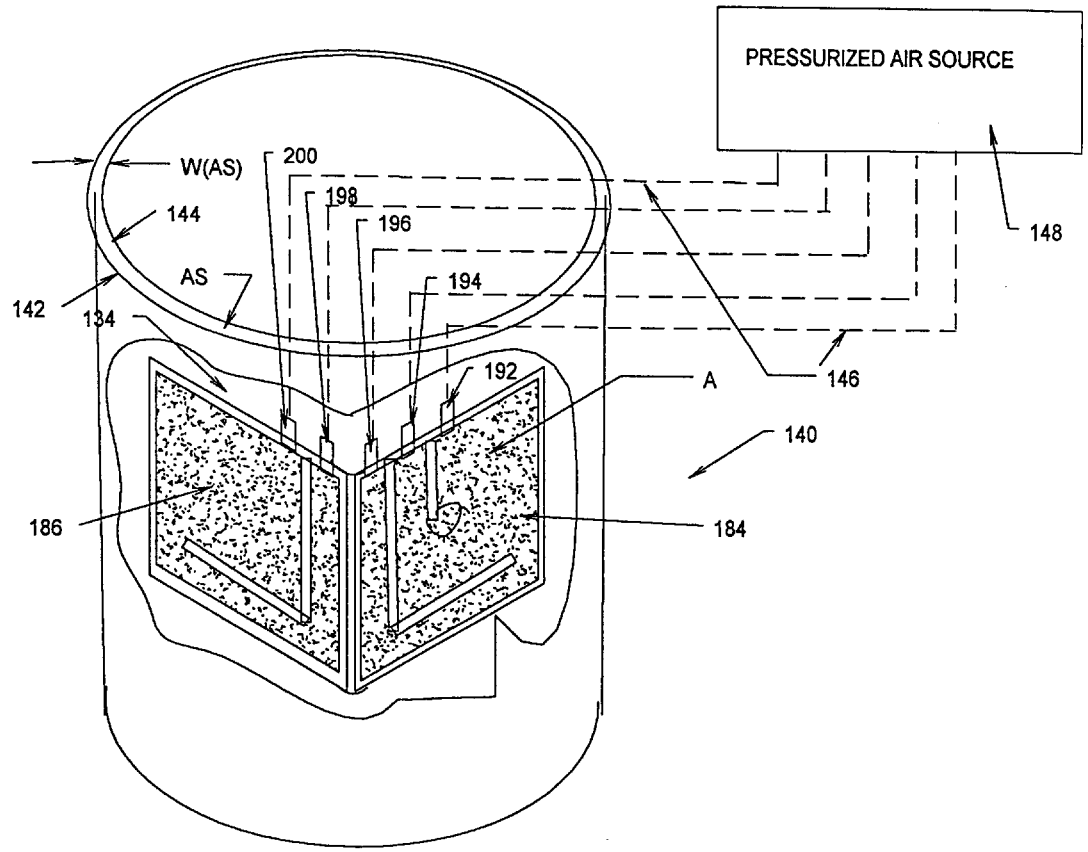
FIG. 24 is a front, largely schematic view of a fixture to apply pressure to the interior of the third bag subassembly, while the plastic materials of its walls are in a heat-softened condition.

As FIG. 24 shows, the restraining fixture 140 consists of two curved plates 142 and 144, which form an arcuate space AS between them. The space AS has a width W(AS) that corresponds to the width WG of the rotor gap 180 that the container 94 will occupy during centrifugation (as FIG. 18 shows). In addition, the plates 142 and 144 of the fixture 140 are contoured to match the contours of the high-G wall 202 and low-G wall 204 of the gap 180, as FIG. 18 also shows. That is, the plate 142 has the same surface contours of the high-G wall 202, and the plate 144 has the same surface contours of the low-G wall 204. The plates 142 and 144 also possess the same radius of curvature as the high-G and low-G walls 202 and 204, respectively. The curved and contoured plates 142 and 144 of the fixture 140 are maintained at a temperature cooler than the softened sheets 124 and 126, preferably at room temperature. The third phase container subassembly 134 is suspended within the space AS along only the top peripheral seal 188T. The other peripheral seals 188L, 188R, and 188B are not directly supported by the plates 142 and 144.

One or more of the ports 192, 194, and 196, serving the first chamber 184, and one or more of the ports 198 and 200, serving the second chamber 186, are coupled by tubes 146 to a source of pressurized fluid 148, which is preferably air. Those ports 192, 194 or 196 (for the first chamber 184) and ports 198 and 200 (for the second chamber 186) that are not coupled to the source 148 are capped to retain pressurized fluid in the chambers 184 and 186.

As previously described in connection with the container 10, the introduction of pressurized air A into the chambers 184 and 186 causes the heat-softened sheets to expand or billow outward symmetrically (see FIG. 25). The space AS defined by the fixture 140 limits the extent to which the heat-soften sheets 124 and 126 expand. The third stage container subassembly 134 will, upon expansion, gradually conform to the contoured surfaces of the plates 142 and 144.

As interior air pressure A is applied uniformly along the entire unsealed area of the third stage container subassembly 134, the heat-softened sheets 124 and 126 symmetrically extend as they gradually expand to fill the space AS. The extension of the heat-softened sheets 124 and 126 creates a new contoured shape, which is free material stress, that matches the contours of the rotor gap 180.

Figure 25:
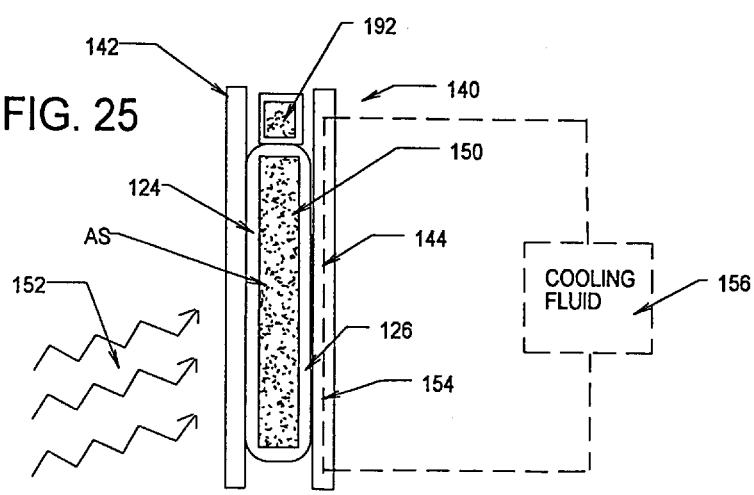
FIG. 25 is a side view of the fixture shown in FIG. 24, showing a fourth bag subassembly, in which the heat-softened walls have been expanded and extended to a three-dimensional shape defined by the fixture.

FIG. 25 shows a fourth stage container subassembly 150, which has acquired the desired shape between the two curved, contoured plates 142 and 144 under the influence of internal air pressure A.

(v) Fifth Phase: Cooling the Extended Wall Material

Assemblage of the container 10 (see FIG. 25) next entails allowing the fourth stage container subassembly 150 to cool while still constrained the within the fixture 140 and subject the application of internal air pressure A. The fourth stage container subassembly 150 can be cooled by an ambient external air flow (shown by arrows 152 in FIG. 25) or a pressurized stream of cooling air. Alternatively or in combination, one or both plates 142 and 144 can include interior passages 154 (shown in phantom lines in FIG. 25) to circulate a cooling fluid from a source 156 (also shown in phantom lines in FIG. 25).

(vi) Final Assembly and Sterilization

When the fourth stage container subassembly 150 has cooled to room temperature, the application of pressure is terminated and the fixture 140 is removed. As FIGS. 14 to 16 show, the previous lay-flat bag subassemblies 128, 132, and 134 have been transformed into to the container 94, which has been extended into a three-dimensional shape to possess a preformed, permanent interior volume that matches the contours of the rotor gap 180.

After removal from the fixture 24, flexible tubing 158 (shown in FIG. 14) can be secured by adhesive or solvent bonding to the appropriate port tubes 192, 194, 196, 198, and 200.

The flexible, three-dimensional container 94 has been created, which can be sterilized by conventional methods, without deformation. Having conventional medical grade polyvinyl chloride material, the container can also be sterilized by expose to ETO or by autoclaving.

During use, the bag 10 or container 94 will maintain its intended predefined three-dimensional geometry, without localized deformation or stress related material fatigue or failure. The combination of internal pressure and heat creates a robust container structure more resistant to stress-related material fatigue or failure than conventional bags made from opposing flat sheets of plastic material, or bags having vacuum formed sides. This attribute makes the bag 10 and container 94 particularly well suited for use in the medical field, where standards against failure and leakage are high.

III. Preferential Extension

The foregoing embodiments show the generally symmetric extension of the side walls of a given container; that is, both side walls are generally extended by the same degree when heated and subject to positive internal pressure. The invention also provides alternative containers 10' (which FIG. 28 exemplifies), in which one side wall sheet 54 is extended to a greater extend than the opposite side wall sheet 52, or when only one side wall sheet 52 or 54 is extended. The container, 10' thereby provides a more asymmetric configuration. The formation of asymmetric containers 10' like that shown in FIG. 28 will, in shorthand, be called preferential or differential extension.

A. Asymmetric Extension Fixture

Figure 26:
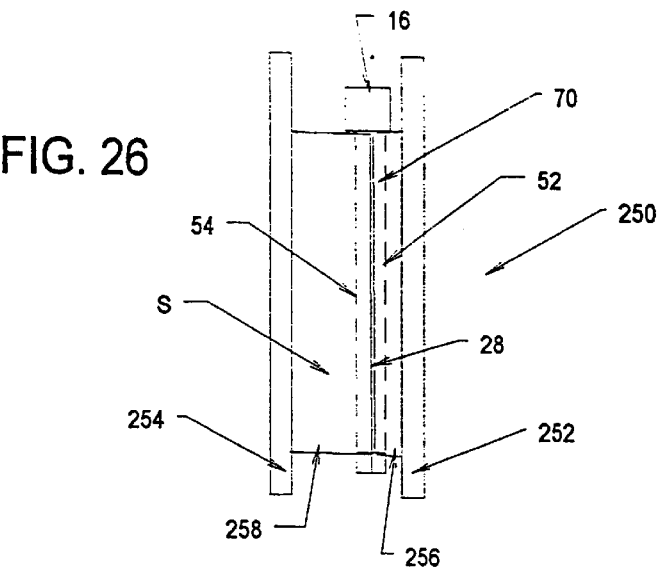
FIG. 26 is a side view of a fixture, which, in use, provides for differential extension of a third bag subassembly to form an asymmetric container.

FIG. 26 shows a heat-softened, third stage bag subassembly 70 (of the type shown in FIGS. 11 and 12) placed in an asymmetric restraining fixture 250. The fixture 250 is configured to cause an asymmetric expansion of the heated sheets 52 and 54 upon introduction of positive pressure into the subassembly 70, as FIG. 27 shows.

As FIG. 26 shows, the restraining fixture 250 consists of opposed parallel plates 252 and 254. Both plates 252 and 254 are maintained at a temperature cooler than the third stage bag subassembly 70, as already explained with respect to the symmetric fixture 76 shown in FIG. 11. Unlike the fixture 76, in which only the top seal region 30 is held by the fixture 76, the parallel plates 252 and 254 of the fixture 250 include opposed seal support flanges 256 and 258. The flanges 256 and 258 hold the entire peripheral seal 28 and interior seal 44 of the subassembly 70 within the fixture 250.

Furthermore, the flanges 256 project from the plate 252 a shorter distance than the flanges 258 project from the plates 254. As a result, the fixture 250 holds the sheet 52 closer to the adjacent plate 252 than the sheet 54 is held relative to its adjacent plate 254.

Figure 27:
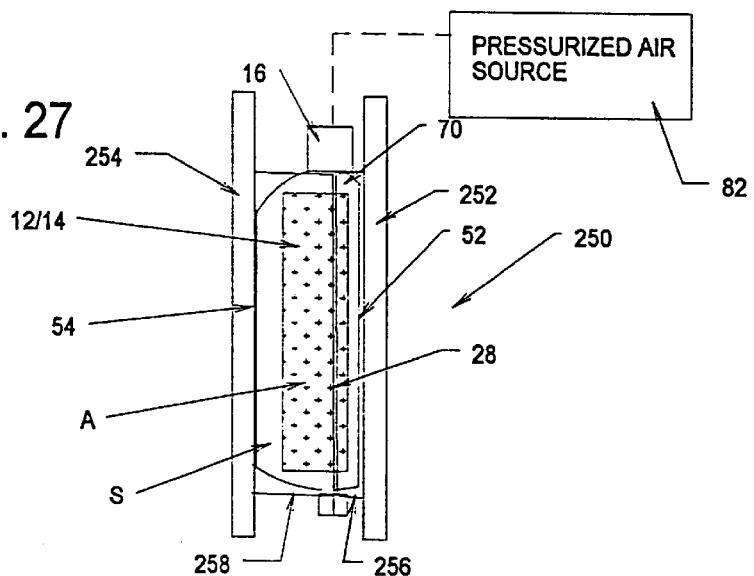
FIG. 27 is a side view of the fixture shown in FIG. 26, as positive pressure is applied to the interior of the third bag subassembly, resulting in differential extension of sheet material.

As FIG. 27 shows, when one or more of the ports 16, 18, and 20 are coupled to a source 82 of pressurized fluid (e.g., pressurized air A), as previously described, the introduction of pressurized air A into the chambers 12 and 14 causes the heat softened sheets 52 and 54 to expand or billow outward. As FIG. 27 shows, expansion of the sheet 52 within the fixture 250 is more limited by its close proximity to the plate 252 than expansion of the sheet 54 toward its adjacent plate 254. The third stage bag assembly 70 will, upon expansion, gradually conform to the space S within the fixture 250. However, the material of the heat-softened sheets 52 and 54 will experience asymmetrically extension in the space S, as sheet 54 will extend to a greater extent that sheet 52. Because the interior fluid pressure is applied uniformly along the entire unsealed area of the third stage bag assembly 70, the extension of the heat-softened material, although asymmetric, still uniformly relieves material stress along the entire unsealed area.

The third stage bag assembly 70 acquires a new, asymmetrically expanded shape in the fixture 250, as shown in FIG. 27. Cooling within the fixture 250 (still subject the application of internal air pressure) completes the asymmetric extension process. The asymmetric subassembly 70 is then ready for final assembly and sterilization, as previously described, to create the asymmetric container 10' shown in FIG. 28.

B. Cooled Asymmetric Extension Fixture

Figure 29:
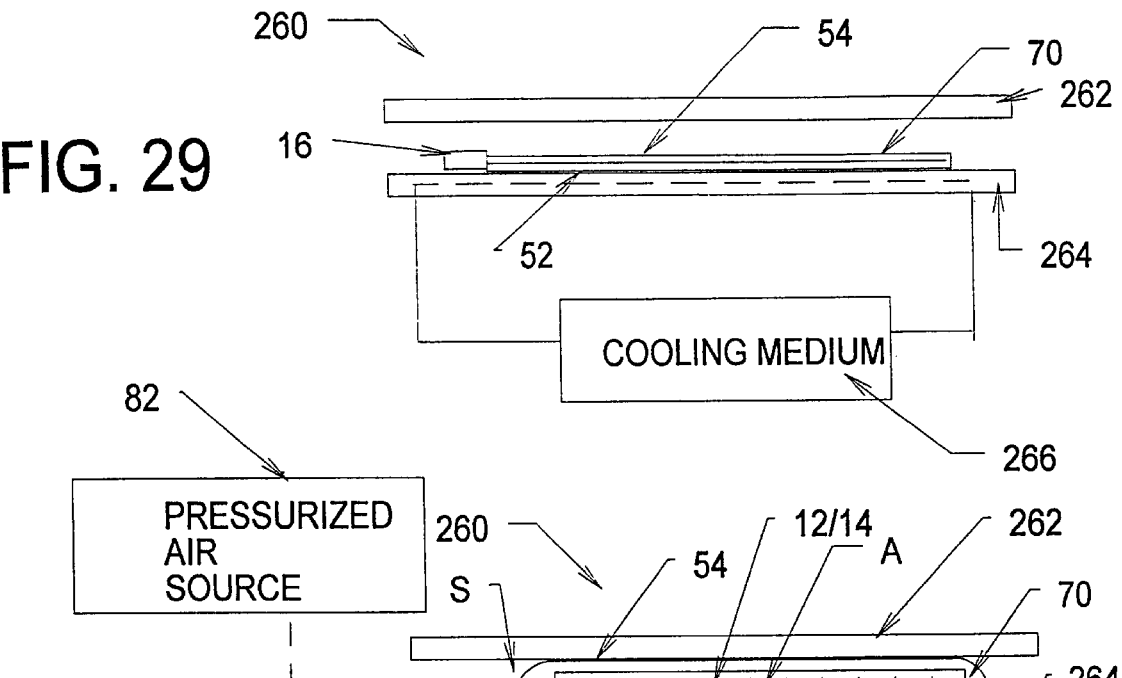
FIG. 29 is a side view of a differentially cooled fixture, which, in use, provides for differential extension of a third bag subassembly to form an asymmetric container.

FIG. 29 shows a heat-softened, third stage bag subassembly 70 (of the type shown in FIGS. 11 and 12) placed in a differentially cooled restraining fixture 260. Like fixture 250, the fixture 260 causes an asymmetric expansion of the sheets 52 and 54 upon introduction of positive pressure into the subassembly 70.

Figure 28:
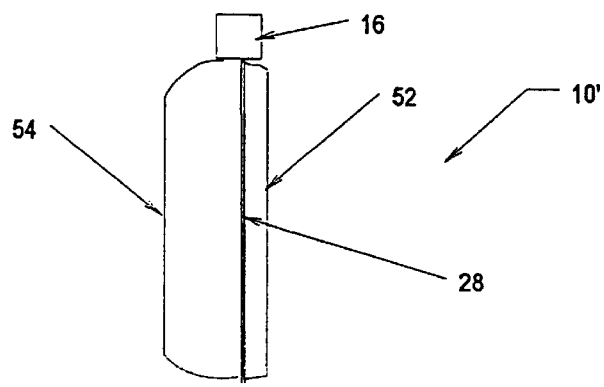
FIG. 28 is an asymmetric container formed as a result of differential extension within the fixture shown in FIG. 26.

As FIG. 28 shows, the restraining fixture 260 consists of opposed horizontal top and bottom plates 262 and 264. Both plates 262 and 264 are maintained at a temperature cooler than the third stage bag subassembly 70. However, the bottom plate 264 is maintained at a lower temperature than the top plate 262, which is above the softening temperature of the sheet material. While there are various ways to differentially cool the plates 262 and 264, in the illustrated embodiment, the bottom plate is maintained at the lower temperature by the circulation of a cooling medium from a source 266.

As FIG. 29 shows, the heat-softened sheet 52 of the subassembly 70 is laid against the differentially cooled bottom plate 264. The heat-softened sheet 54 faces the top plate 262, which is maintained at, e.g., room temperature. The plates 262 and 264 are spaced apart a predetermined amount to allow for extension of the subassembly 70 in the fixture 260.

Figure 30:
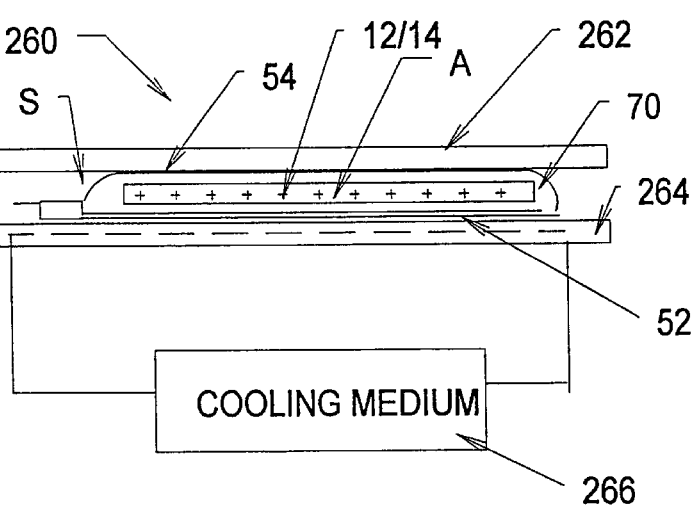
FIG. 30 is a side view of the fixture shown in FIG. 29, as positive pressure is applied to the interior of the third bag subassembly, while under-going differential cooling, resulting in differential extension of sheet material and the formation of an asymmetric container like that shown in FIG. 28.

As FIG. 30 shows, the introduction of pressurized air A into the chambers 12 and 14 causes the heat-softened sheet 54 to expand or billow outward, toward the top plate 262. However, extension of the sheet 52 is prevented or at least minimized, compared to extension of the sheet 54, because the sheet 52 is differentially cooled below its softening point. The third stage bag assembly 70 will, upon expansion, conform to the space S within the fixture 260. However, due to differential cooling, the material of the heat-softened sheets 52 and 54 will experience asymmetrically extension in the space S. As FIG. 30 shows, the heat-softened sheet 54 will expand to a greater extent than cooled sheet 52. Because the interior fluid pressure is applied uniformly along the entire unsealed area of the third stage bag assembly 70, the extension of the heat-softened material, although asymmetric, still uniformly relieves material stress along the entire unsealed area.

As FIG. 30 shows, the third stage bag assembly 70 acquires a new, asymmetrically expanded shape in the fixture 260. Cooling of the top plate 264 while the asymmetrically expanded subassembly 70 is constrained the within the fixture 260 and subject the application of internal air pressure, completes the asymmetric extension process. The asymmetric subassembly 70 is ready for final assembly and sterilization, as previously described, to create an asymmetric container 10' like that shown in FIG. 28.

EXAMPLE

Four three-dimensional bags of the type shown in FIGS. 1 to 3 were made by heat and pressure forming, using EVA sheet materials, in the manner previously described (which will be called in shorthand the "Pressure Formed Bags").

Four three-dimensional bags were made by forming cavities in vacuum formed plastic sheets made from both EVA materials of comparable thickness to the Pressure Formed Bags. The vacuum formed sheets were peripherally joined together by heat seals created by applying radio frequency energy. These bags will be called in shorthand the "Vacuum Formed Bags."

The Pressure Formed Bags and the Vacuum Formed Bags had generally the same dimensions and interior volumes.

The Pressure Formed Bags and the Vacuum Formed Bags were pressure tested to failure. The following Table summarizes the results.

TABLE 1

Pressure Tests of Pressure Formed Bags and Vacuum Formed Bags

| Bag Type | Average Pressure at Which Failure Occurred |
| --- | --- |
| Pressure Formed Bags 1 to 4 (EVA) | 82 PSI |
| Vacuum Formed Bags 1 to 4 (EVA) | 65 PSI |

Table 1 demonstrates that the Pressure Formed Bags did not fail at pressures at which the Vacuum Formed Bags failed.

The Vacuum Formed Bags all failed at corners formed during the vacuum forming process. These vacuum-formed corners represented areas where the plastic material had been over-stretched and thus prone to premature failure when subjected to stress.

The use of heat and uniform interior pressure, as described herein, uniformly relieves material stress in the Pressure Formed Bags.

It should be appreciation that variations to the described structures and processes can be made while keeping many of the important features of the invention.

The features of the invention are set forth in the following claims.

What is claimed is:

1. A method for making a flexible container comprising the steps of providing first and second flexible sheets of plastic material which softens in response to exposure to heat, the first and second flexible sheets having top, side and bottom peripheral edges, forming a first seal region joining the peripheral side and bottom edges along a plane to create an interior chamber in the container, the peripheral top edge of the container being left unsealed, locating a port tube body between the first and second flexible sheets in the unsealed peripheral top edge, forming a second seal region joining the peripheral top edge along the plane and joining the port tube body within the peripheral top edge, the port tube body providing fluid flow communication with the interior chamber through the second seal region, after forming the first and second seal regions, softening the first and second flexible sheets by exposure to heat, forming heat-softened first and second flexible sheets, and applying positive pressure inside the interior chamber through the port tube body to form in the heat-softened first and second flexible sheets stress-relieved regions extending outside the plane and overlying the interior chamber.

2. A method according to claim 1 wherein the step of forming the first seal region includes the step of forming an interior seal joining the flexible sheets together along the plane to form first and second compartments in the interior chamber, wherein the locating step includes locating first and second port tube bodies between the first and second flexible sheets in the unsealed peripheral top edge, wherein the step of forming the second seal region includes the step of joining the peripheral top edge along the plane and joining the first and second port tube bodies within the peripheral top edge, the first and second port tube bodies providing fluid flow communication, respectively, with the first and second compartments of the interior chamber through the second seal region, and wherein the step of applying positive pressure includes applying positive pressure inside the first and second compartments of the interior chamber through the first and second port tube bodies, respectively, to form stress-relieved regions that overlie each of the first and second compartments.

3. A method according to claim 2 wherein the interior seal includes an interruption providing fluid flow communication between the first and second compartments.

4. A method according to claim 1 wherein the plastic material is selected from a group consisting essentially of polyvinyl chloride, polyethylene, polypropylene, ethylene-vinyl-acetate, fluropolymers, or copolymers of these materials.

* * * * *